US012774307B2

(12) United States Patent
Jiang et al.

(10) Patent No.: US 12,774,307 B2
(45) Date of Patent: Oct. 27, 2026

(54) MOLECULAR PEPTIDE MUTANT WITH A HIGH ESTER BOND FORMATION EFFICIENCY

(71) Applicant: NANJING TECH UNIVERSITY, Nanjing (CN)

(72) Inventors: Ling Jiang, Nanjing (CN); Yao Chen, Nanjing (CN); Yujin Chen, Nanjing (CN); Liying Zhu, Nanjing (CN); Wei Liu, Nanjing (CN)

(73) Assignee: NANJING TECH UNIVERSITY, Nanjing (CN)

( * ) Notice: Subject to any disclaimer, the term of this patent is extended or adjusted under 35 U.S.C. 154(b) by 2 days.

(21) Appl. No.: 18/255,368

(22) PCT Filed: Aug. 30, 2022

(86) PCT No.: PCT/CN2022/115683

§ 371 (c)(1),
(2) Date: Jun. 1, 2023

(87) PCT Pub. No.: WO2024/016429

PCT Pub. Date: Jan. 25, 2024

(65) Prior Publication Data

US 2024/0376160 A1 Nov. 14, 2024

(30) Foreign Application Priority Data

Jul. 22, 2022 (CN) ......................... 202210870801.8

(51) Int. Cl.
*C12N 15/70* (2006.01)
*C07K 14/315* (2006.01)
*C12R 1/19* (2006.01)

(52) U.S. Cl.
CPC ............ *C07K 14/315* (2013.01); *C12N 15/70* (2013.01); *C12R 2001/19* (2021.05)

(58) Field of Classification Search
CPC ...................................................... C12N 15/70
See application file for complete search history.

(56) References Cited

U.S. PATENT DOCUMENTS

2018/0244730 A1 8/2018 Howarth

FOREIGN PATENT DOCUMENTS

| | | | |
|---|---|---|---|
| CN | 106591345 | A | 4/2017 |
| CN | 108715846 | A | 10/2018 |
| CN | 110709412 | A | 1/2020 |
| CN | 111954683 | A | 11/2020 |
| CN | 113214369 | A | 8/2021 |
| CN | 114685677 | A | 7/2022 |
| WO | 2018197854 | A1 | 11/2018 |

OTHER PUBLICATIONS

Thermo Fisher Scientific (Dialysis Methods for Protein Research; Retrieved for Date: Mar. 8, 2021). (Year: 2021).*
EDT23863.1; putative surface anchored protein [*Clostridium perfringens* B str. ATCC 3626], BioCollection Taxonomy Date: Mar. 24, 2008) (Year: 2008).*
Kwon et al (Autocatalytically generated Thr-GIn ester bond cross-links stabilize the repetitive Ig-domain shaft of a bacterial cell surface adhesin; PNAS, 2014, 11(4):1367-1372) (Year: 2014).*
Novagen (pET-22b(+) Vector, Retrieved from Date: Nov. 9, 2021). (Year: 2021).*
Yosaatmadja (Ester bond formation in bacterial adhesins; Thesis, University of Auckland Research Repository, Aug. 2018). (Year: 2018).*
Nakajo et al (Purification and Characterization of a Novel Brain-Specific 14-kDa Protein; Journal of Neurochemistry, 1990, 55(6): 2031-2038). (Year: 1990).*
Young et al (Molecular Superglues: Discovery and Engineering Orthogonalization; Chapter 6, Protein Nanotechnology: Protocols, Instrumentation, and Applications, Methods in Molecular Biology, 2020, 2073:85-99). (Year: 2020).*
Hanna Kwon, et al., Autocatalytically generated Thr-Gln ester bond cross-links stabilize the repetitive Ig-domain shaft of a bacterial cell surface adhesin, Proceedings of the National Academy of Sciences, 2014, pp. 1367-1372, vol. 111, No. 4.
Xinzhe Wang, et al., Advances in protein cyclization, Chinese Journal of Biotechnology, 2016, pp. 430-439, vol. 32, No. 4.
Miriam Walden, et al., An internal thioester in a pathogen surface protein mediates covalent host binding, eLife, 2015, pp. 1-24, vol. 4, e06638.
NCBI Reference Sequence: WP_164801176.1, thioester-forming surface-anchored protein, partial [Clostridium perfringens], NCBI GenBank, 2020, pp. 1-2.

* cited by examiner

*Primary Examiner* — Neil P Hammell
*Assistant Examiner* — Qiwen Su-Tobon
(74) *Attorney, Agent, or Firm* — Bayramoglu Law Offices LLC

(57) ABSTRACT

The invention relates to a molecular peptide mutant with a high ester bond formation efficiency, the amino acid sequence of which is as shown in SEQ ID NO: 1. The invention introduces mutations at three sites on the basis of not affecting the spatial structure of Catcher, and through three mutations, obtains the Catcher mutant EBCatcher, which significantly improves the stability of the Catcher in water solution and can improve the binding efficiency to EBTag.

9 Claims, 2 Drawing Sheets

Specification includes a Sequence Listing.

| | |
|---|---|
| Catcher | TIPEVKEGTLKTTVAADGVNGSSEKEALVS**F**ENSKDGVDVKDTIDYKD |
| EBCatcher(SEQ ID NO:1) | TIPEVKEGTLKTTVAADGVNGSSEKEALVS**Y**ENSKDGVDVKDTIDYKD |
| Catcher | LVANEKYNLTGKLMHVKDDGSLEEVATKTTEVTAVENGSGQWELD**F**GN |
| EBCatcher | LVANEKYNLTGKLMHVKDDGSLEEVATKTTEVTAVENGSGQWELD**I**GN |
| Catcher | **Q**KLQVGEKYVVFENAESVENLIDTDNNYE |
| EBCatcher | **E**KLQVGEKYVVFENAESVENLIDTDNNYE |

Fig. 1

MOLECULAR PEPTIDE MUTANT WITH A HIGH ESTER BOND FORMATION EFFICIENCY

SEQUENCE LISTING

The present application contains a Sequence Listing which has been submitted in XML format via EFS-Web and is hereby incorporated by reference in its entirety. Said XML copy is named 20230628_002149P-WOUS_SequenceST26.xml, created on 06/28/2023, and is 2,273 bytes in size.

TECHNICAL FIELD

The present invention pertains to the field of design of molecular peptides and particularly relates to a molecular peptide mutant with a high ester bond formation efficiency.

BACKGROUND ART

In 2014, Edward N. Baker et al discovered the formation of isopeptide bond Ig-like protein between Thr-Gln and conducted structural analysis. The PDB ID of its crystal structure is 4ni6. In 2017, the team separated the protein into Catcher and Tag. In an acidic environment, Thr11 of the Catcher and Gln14 of the Tag can form a covalent bond (ester bond), but glycerol and $CaCl_2$ need to be added to the system. Different from ordinary molecular peptide pairs, the pH of the environment needs to be adjusted to 8.0, and the ester bond can be hydrolyzed after glycerol and $Ca^{2+}$ are dialyzed out. It is applied in protein separation and other fields, but the low covalent bond formation efficiency will hinder its further application.

SUMMARY OF THE INVENTION

Through rational design, the present invention modifies Catcher to obtain the mutant named EBCatcher, which can quickly form a covalent bond with EBTag (which is not mutated, here we name the original Tag as EBTag).

The present invention introduces three mutations on the Catcher to significantly improve the covalent bond formation efficiency between Tag and Catcher. In the present invention, the Catcher obtained from modification is called EBCatcher, and the Tag is not mutated, here we name it EBTag.

A molecular peptide mutant with a high ester bond formation efficiency, the amino acid sequence of which is as shown in SEQ ID NO: 1.

Another objective of the present invention is to provide a gene sequence encoding the molecular peptide mutant according to claim 1.

Another objective of the present invention is to provide an application of the molecular peptide mutant in protein separation.

Another objective of the present invention is to provide a method for purifying the molecular peptide mutant, comprising the following steps:

(1) introducing the gene sequence of the molecular peptide into a vector to construct a recombinant plasmid, and introducing the recombinant plasmid into a host bacterium;

(2) culturing the host bacterium containing the recombinant plasmid till $OD_{600}$=0.6-0.8, and then adding IPTG for induction;

(3) taking and centrifuging a bacteria solution after the end of the induction, collecting cells, adding a phosphate buffer solution for resuspension, and carrying out ultrasonication; and (4) carrying out ultracentrifugation of the crushed liquid, taking the supernatant, and carrying out purification dialysis to obtain purified protein.

Preferably, in the (1), the vector is pET-22b.

Preferably, the restriction enzyme sites ligated to the vector are Nde I and Xho I.

Preferably, in the (1), the host bacterium is *E. coli* BL21(DE3).

Preferably, in the (2), *E. coli* BL21(DE3) containing the recombinant plasmid is cultured in an LB medium.

Preferably, in the (4), the supernatant is subjected to protein purification in Ni-NTA resin.

Preferably, the purified protein is dialyzed in a 3,000 Da dialysis bag for 24-26 h.

The modified EBCatcher still can form an isopeptide bond with EBTag, but the covalent bond formation efficiency is improved significantly.

BRIEF DESCRIPTION OF THE DRAWINGS

FIG. 1 shows sequence alignment of Catcher and EBCatcher. The EBCatcher amino acid sequence shown in FIG. 1 is identified as SEQ ID NO: 1.

DETAILED DESCRIPTION

Figure 2:
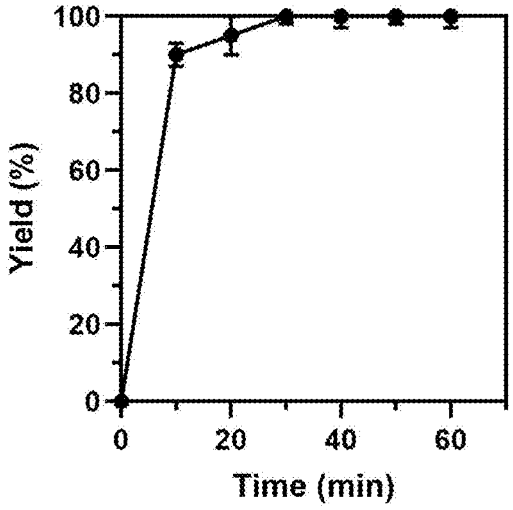
FIG. 2 shows the ligation efficiencies of EBCatcher-GFP and EBTag-GFP.

The original protein crystal structure in the embodiments is obtained from a PDB database, and the PDB ID is 4ni6.

Embodiment 1

This embodiment specifically describes a mutant design method.

The amino acid sequence of the Catcher is subjected to a mutation design by observing the original protein crystal structure. F31 is located at the calcium ion binding site, a hydroxyl group is introduced on Phe to become Tyr (F31Y), which improves local *hydrophilia* without changing the spatial structure, reduces free energy in a water solution and enhances stability; while F94 is located inside the Catcher, and mutates Phe into Ile with a smaller side chain volume, which can effectively reduce internal steric hindrance and improve folding stability; a polar amino acid Glu is introduced at the Q97 site to reduce the folding energy in a water solution without affecting the structure by and large. Through three joint mutations, the stability of EBCatcher in a water solution can be improved to a great extent and the binding efficiency to EBTag can be improved.

Embodiment 2

This embodiment specifically describes a mutant purification method.

Carry out whole-gene synthesis of the mutated molecular peptide in Sangon Biotech (Shanghai) Co., Ltd. and add a GFP on EBTag and EBCatcher simultaneously to increase the molecular weight. Clone on a vector pET-22b to obtain a recombinant plasmid pET-22b-EBCatcher-GFP, wherein the restriction enzyme sites are Nde I and Xho I, and the host is *E. coli* BL21 (DE3). The recombinant vector of EBTag-GFP is pET-22b-EBTag-GFP, and the restriction enzyme sites and host are the same as those of EBCatcher-GFP.

Culture *E. coli* BL21 (DE3) containing the recombinant plasmid in an LB medium at 37° C. till $OD_{600}$=0.6, add 1 M IPTG till a final concentration of 0.5 mM, and induce at 20° C. for 12 h.

The cells are obtained after 12,000 rpm centrifugation after the end of the induction, and 4 mL phosphate buffer is added to resuspend the cells, and 350 W ultrasonication is carried out for 15 min.

The surpernatant is obtained after 12,000 rpm ultracentrifugation at 4° C. for 20 min, and the protein is purified using Ni-NTA resin. The purified protein is dialyzed using a 14,000 Da dialysis bag for 26 h and kept for future use.

Embodiment 3

This embodiment has only the following difference from Embodiment 1:

The *E. coli* BL21 (DE3) containing the recombinant plasmid is cultured in an LB medium at 37° C. till $OD_{600}$=0.8, and 1 M IPTG is added till a final concentration of 0.5 mM to induce protein expression at 25° C. for 12 h.

Embodiment 4

This embodiment tests the ligation efficiencies of EBCatcher-GFP and Catcher-GFP.

Buffer B is a pH 8.0 0.1M phosphate buffer solution with 500 mM NaCl and 300 mM imidazole;

The 1 mL Ni-NTA pre-packed column is purchased from Sangon Biotech (Shanghai) Co., Ltd. Other reagents are all commercially available.

SDS-PAGE protein gel electrophoresis method:

Mix 30 μL of sample with 10 μL of 4× loading buffer, preserve the temperature in a 100° C. metal bath for 10 min, reduce the temperature to 4° C. after the preservation and then centrifuge at 1000-12000 rpm. Use an SDS-PAGE protein gel kit to prepare 12% separation gel and 5% concentration gel. Load 10 μL of the prepared sample, at a voltage of 120 V and an electrophoresis time of 120 min. Stain with a Coomassie brilliant blue staining solution for 60-120 min, and decolor with a destaining solution until the background is transparent. Photograph in a gel imager and perform strip density analysis by using ImageJ to obtain the ligation efficiency. The SDS-PAGE protein gel kit was purchased from Beijing Solarbio Science & Technology Co., Ltd. and other reagents are all commercially available.

Figure 3:
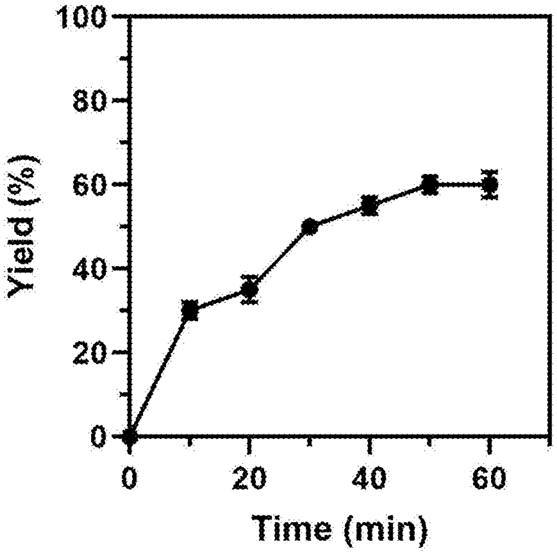
FIG. 3 shows the ligation efficiencies of Catcher-GFP and EBTag-GFP.

The results are as shown in FIG. 2 and FIG. 3 (the vertical coordinate is a product of protein complex). It can be seen that the molecular peptide mutant EBCatcher obtained through calculation in the present invention not only has the ability to form an isopeptide bond with EBTag and also significantly increases the covalent bond formation efficiency. Further, the result of protein-induced expression in Embodiment 2 is slightly different from that in Embodiment 1, but it does not have an obvious impact on the ultimate covalent bond formation efficiency.

SEQUENCE LISTING

```
Sequence total quantity: 1
SEQ ID NO: 1            moltype = AA  length = 125
FEATURE                 Location/Qualifiers
source                  1..125
                        mol_type = protein
                        note = Artificial
                        organism = unidentified
SEQUENCE: 1
TIPEVKEGTL KTTVAADGVN GSSEKEALVS YENSKDGVDV KDTIDYKDLV ANEKYNLTGK  60
LMHVKDDGSL EEVATKTTEV TAVENGSGQW ELDIGNEKLQ VGEKYVVFEN AESVENLIDT  120
DNNYE                                                              125
```

Experimental group: The EBTag-GFP and EBCatcher-GFP are mixed as specified in Embodiment 1 at a ratio of 1:1 according to a concentration of 10 μM in 0.1 M pH 6.0 phosphate buffer (containing 20% glycerol and 100 μM $CaCl_2$). The reaction will take place at 20° C. for 60 min, and a sample is collected every 10 min in this period. The SDS-PAGE is performed to measure the ligation efficiency.

Control group: The whole-gene synthesis of Catcher-GFP is from Sangon Biotech (Shanghai) Co., Ltd. Other methods are the same as those adopted in Embodiment 2 and the experimental group.

Of them, the protein purification method is as follows:

Drain the 20% ethanol protective liquid in the 1 mL Ni-NTA pre-packed column and add 3-4 column volumes of Buffer A to replace the ethanol in the packing. Pour the ultracentrifuged protein sample into the packing and drain it. Then add 3-4 column volumes of Buffer A for elution to remove miscellaneous protein adsorbed on the packing. Then add 3-4 column volumes of Buffer B to elute the target protein.

Buffer A is a pH 8.0 0.1M phosphate buffer solution with 500 mM NaCl and 20 mM imidazole;

What is claimed is:

1. A molecular peptide mutant, wherein the molecular peptide mutant consists of the amino acid sequence set forth in SEQ ID NO: 1 and, wherein the molecular peptide mutant forms ester bonds.

2. A method for purifying the molecular peptide mutant according to claim 1, wherein the method comprises the following steps:

(1) introducing agene sequence encoding the molecular peptide mutant into a vector to construct a recombinant plasmid, and introducing the recombinant plasmid into a host bacterium;

(2) culturing the host bacterium containing the recombinant plasmid till OD600=0.6-0.8, and then adding isopropyl β-D-1-thiogalactopyranoside (IPTG) for induction;

(3) taking and centrifuging a bacteria solution after the end of the induction, collecting cells, adding a phosphate buffer solution for resuspension, and carrying out ultrasonication to obtain a crushed liquid; and (4) carrying out ultracentrifugation of the crushed liquid, collecting a supernatant, and carrying out protein purification and dialysis to obtain purified protein.

3. The method according to claim 2, wherein in the (1), the vector is pET-22b.

4. The method according to claim 2 wherein, in step (1), the gene sequence is ligated to the vector using restriction enzyme sites NdeI and XhoI.

5. The method according to claim 2, wherein, in step (1), the host bacterium is *Escherichia coli* (*E. coli*) BL21 (DE3).

6. The method according to claim 5, wherein in step (2), DE3 containing the recombinant plasmid is cultured in a lysogeny broth (LB) medium.

7. The method according to claim 2, wherein in step (4), the supernatant is subjected to protein purification in nickel-nitrilotriacetic acid (Ni-NTA) resin.

8. The method according to claim 2, wherein the purified protein is dialyzed in a 3,000 dalton dialysis bag for 24-26 hours.

9. A gene sequence encoding a molecular peptide mutant, wherein the molecular peptide mutant consists of the amino acid sequence set forth in SEQ ID NO: 1.

* * * * *